US011097039B2

(12) United States Patent
Garbez et al.

(10) Patent No.: US 11,097,039 B2
(45) Date of Patent: Aug. 24, 2021

(54) SUBMERSIBLE BREAST PUMP PROTECTION MECHANISM FOR A BREAST MILK COLLECTION DEVICE WITH SELF-CONTAINED RESERVOIR

(71) Applicant: Dao Health, El Dorado Hills, CA (US)

(72) Inventors: Dan Garbez, El Dorado Hills, CA (US); Stella Dao, El Dorado Hills, CA (US); Dave Paul, Scotts Valley, CA (US); Ben Sutton, Scotts Valley, CA (US)

(73) Assignee: DAO Health, El Dorado Hills, CA (US)

( * ) Notice: Subject to any disclaimer, the term of this patent is extended or adjusted under 35 U.S.C. 154(b) by 138 days.

(21) Appl. No.: 16/293,869

(22) Filed: Mar. 6, 2019

(65) Prior Publication Data
US 2019/0224389 A1    Jul. 25, 2019

Related U.S. Application Data

(62) Division of application No. 15/205,740, filed on Jul. 8, 2016, now Pat. No. 10,258,723.

(51) Int. Cl.
*A61M 1/06* (2006.01)
*A61M 1/00* (2006.01)
*A61M 39/22* (2006.01)

(52) U.S. Cl.
CPC .......... *A61M 1/066* (2014.02); *A61M 1/0037* (2013.01); *A61M 1/06* (2013.01); *A61M 1/062* (2014.02); *A61M 1/064* (2014.02); *A61M 39/22* (2013.01); *A61M 2205/7536* (2013.01)

(58) Field of Classification Search
CPC ........ A61M 1/062; A61M 1/06; A61M 1/064; A61M 1/066
See application file for complete search history.

(56) References Cited

U.S. PATENT DOCUMENTS

| | | | |
|---|---|---|---|
| 2005/0043677 A1* | 2/2005 | Kelly | A61M 1/0031 604/74 |
| 2008/0208116 A1* | 8/2008 | Dao | A61M 1/06 604/74 |
| 2015/0265753 A1* | 9/2015 | Prentice | A61M 1/0037 604/74 |

* cited by examiner

*Primary Examiner* — Emily L Schmidt
(74) *Attorney, Agent, or Firm* — Rockman Videbeck & O'Connor

(57) ABSTRACT

A breast milk collection device includes a reservoir volume and an adaptor having one end to receive a woman's breast. The adaptor has a drip tube communicating with the reservoir. A source of cyclical application and relief of vacuum force is applied to the woman's breast located in the adaptor for the expression of breast milk. A one-way assembly permits breast milk to enter the reservoir and to submerge the valve element. The valve assembly includes a flexible barrier having an interior hollow chamber in fluid communication with said cyclical source of vacuum force and relief pressure, the flexible barrier fluidly isolating the source from the reservoir. The flexible barrier inflatably expands when relief pressure is applied to the interior of the flexible barrier, the flexible barrier becoming deflated when a vacuum force is applied to the hollow interior of the flexible barrier.

3 Claims, 6 Drawing Sheets

SUBMERSIBLE BREAST PUMP PROTECTION MECHANISM FOR A BREAST MILK COLLECTION DEVICE WITH SELF-CONTAINED RESERVOIR

This invention is a divisional of non-provisional application Ser. No. 15/205,740, filed Jul. 8, 2016, the contents of which are incorporated herein by reference and claims priority of application Ser. No. 15/205,740 filed Jul. 8, 2016, the contents of which are incorporated herein by reference.

This invention relates to the field of human breast milk collection devices and more specifically, to naturally shaped and hands-free breast milk collection devices which can fit discreetly within a mother's existing or nursing brassiere, including an integrated submersible breast pump protection mechanism to prevent milk from entering the suction source supply tubing.

BACKGROUND OF THE INVENTION

Breast pumps are well known, but the field of breast pump devices with self-contained breast milk reservoirs which can be used discreetly by fitting them within a woman's brassiere, often under ordinary clothing so that a woman can use a breast pump around others discreetly, is relatively new. The only known devices in this field, upon which this invention improves, are taught in U.S. Pat. Nos. 7,559,915 and 8,118,772 (Dao, Garbez), and U.S. Pat. No. 8,702,646 (Dao, Garbez, Paul, Sutton), all commonly assigned, the disclosures of which patents are incorporated by reference herein.

To provide adequate milk collection capacity for lactating women using a breast pump, some presently available breast milk reservoir devices are large, and when placed in a brassiere give a lactating woman an enhanced appearance. These breast milk collection devices are frequently used by a lactating woman underneath her clothing and in the presence of others. An embodiment of these devices utilizes a flap valve between the vacuum source and the stored milk, and the devices reach their maximum collection capacity once the collected milk in the reservoir reaches the bottom of the flap valve.

The risk from overfilling above the level of the flap valve is that when the pump is turned off, the valve may not prevent the undesirable backflow of milk into the breast funnel. This constraint leaves possibly more than half the potential volume of the reservoir unused.

U.S. Pat. No. 8,118,772 discloses in an embodiment a breast milk collection device that includes a flexible barrier between the source of suction force and the milk collected in the reservoir. In this device, the milk in the reservoir can migrate from the reservoir into the interior of the flexible barrier when the vacuum source tube is removed and the collection device is inverted to pour collected milk out of the reservoir into a suitable storage container. The interior of the balloon-shaped flexible barrier of the '772 patent would be practically difficult to clean after each use. To prevent milk from entering the flexible barrier of the '772 patent, the funnel-shaped adapter would have to be detached from the reservoir housing before removing the milk from the reservoir, leading to potential undesirable splashing of the milk. Further, in the milk collection device of the '772 disclosure, the vacuum force tube has to be removed from the breast milk collection device for milk to be transferred out of the reservoir.

SUMMARY OF THE INVENTION

The present invention is an improved barrier which is submersible for use in combination with a submersible valve system deployed in a compact and hands-free human breast milk collection device that fits into a mother's existing nursing or standard brassiere. The device which contains this improved barrier and valve system can be attached to a conventional electric or manual vacuum pump for milk collection. The invention in an embodiment comprises a unique flexible barrier system which is located in the interior of the milk collection reservoir. A breast adaptor including a funnel-shaped inlet is coupled to the reservoir, such that when the breast is inserted into the breast adaptor, breast milk is expressed through a fluid passageway into the reservoir through a unique valve system and the milk is stored in the reservoir until the device is removed and the collected milk emptied into a container. In an embodiment, the flexible barrier is inflatable and deflatable, and is sealingly mounted on a portion of the exterior of the funnel-shaped adaptor. The interior of the barrier comprises an expandable and contractable chamber connected to an external source of cyclical suction force and relief pressure. The flexible barrier completely isolates the external suction source from the milk in the reservoir, and prevents the collected milk in the reservoir from flowing back into the breast adaptor or back into the external suction source.

The cyclical application of suction force and relief pressure to the chamber formed by the flexible barrier alternately expands and contracts the barrier as the suction force is variably and cyclically applied to the chamber and then relieved. When the maximum suction, or negative force is applied to the chamber, the flexible chamber collapses, creating an increase in the volume of a rigid barrier housing, and a corresponding drop in pressure in the rigid barrier housing and in the funnel. This applies a suction force to the nipple in the funnel, withdrawing milk from the breast. The milk flows through the fluid passageway of the valve assembly, and is deposited in the reservoir through a one-way valve system when suction is relieved as the cycle reverses and pressure is supplied into the chamber, and consequently into the funnel, forcing the milk through the one-way valve. In the present embodiment, the valve continues to function as the level of milk in the reservoir rises and submerses the one-way valve.

As the suction force is cyclically relieved or released, the pressure in the internal chamber of the flexible barrier increases, expanding the chamber and increasing the pressure in the milk-receiving assembly comprised of the funnel and valve system located inside the reservoir, and forcing the milk through the one-way valve and into the reservoir itself. Upon the cyclical application of the alternating vacuum force and positive pressure, the process repeats itself.

In an illustrated embodiment of the present disclosure, the inflatable/deflatable flexible barrier creates a complete barrier between the source of vacuum force and pressure cyclically introduced to the reservoir housing, and the milk collected in the reservoir. As a result, milk migration into the vacuum tube, or into the vacuum pump, or into the interior of the flexible barrier itself is totally prevented. Of prime importance is the protection of the vacuum pump from the potentially damaging effects of milk entering the operating parts of the pump. In addition, the presently disclosed barrier system allows the vacuum force supply tube to remain attached to the reservoir housing when milk is being poured from the reservoir through an integral pour spout and into a suitable storage container for subsequent use. In addition, the flexible barrier of the present disclosure can be removed and inverted for ease of cleaning, and the construction and location of the barrier allows a maximum amount of milk to be collected in the reservoir. The present combined flexible barrier and valve system continue to function when both are submerged in the milk collected in the reservoir.

The breast milk collection device further includes a separate pouring spout on the exterior rim of the funnel-shaped adaptor, which spout communicates directly between the interior chamber of the reservoir and the exterior of the milk collection device. Thus, when the reservoir is full or near full of breast milk, the milk can be poured through the spout and into a suitable container without removing the vacuum force tube from the device. Additionally, as milk is poured from the reservoir as the device is in an inverted position, ambient air enters the reservoir through the valve to displace the decreased volume of the poured milk, allowing the milk to be poured from the reservoir through the spout in a smooth, uninterrupted flow stream.

In an alternate embodiment, the flexible barrier is replaced with a fixed hydrophobic, washable filter that prevents the flow of liquid through the filter, but allows air through the filter. This embodiment will use a fixed shape filter that allows the cyclical suction or vacuum force and relief pressure to be applied to the breast, while simultaneously preventing milk from migrating to the suction tubing or to the vacuum pump.

BRIEF DESCRIPTION OF THE DRAWINGS

The invention will be more fully understood by reference to the following drawings which are for illustrative purposes only.

DETAILED DESCRIPTION OF THE ILLUSTRATED EMBODIMENT

The breast milk collection device with a self-contained reservoir, as described herein and in U.S. Pat. Nos. 7,559,915; 8,188,772 and 8,702,646 (incorporated by reference herein) significantly improves a lactating woman's ability to express and pump breast milk by providing a device that can be used by the lactating woman at a stationary place, such as while at work, in a vehicle with a power adaptor, or other public and private places with a minimum of interference or immodesty, and relative minor disruption to the lactating woman's normal activities. In addition, the present invention can function as a passive breast milk collection reservoir when a breast pump is not connected to the reservoir device.

The inventive combination barrier and one-way valve assembly structure of the present invention is submersible in the collected breast milk in the reservoir, and functions to allow breast milk to enter the reservoir from a drip tube and valve assembly connected to the cyclic application and relief of vacuum force to the drip tube during a cessation or relief of the vacuum force application cycle, while at the same time preventing the milk from entering the drip tube or vacuum source from the reservoir during the vacuum force application or relief segments of the cycle. In this manner, the pump providing the vacuum force to the interior of the reservoir is totally isolated from the milk in the reservoir, protecting the vacuum pump from the effects of liquid corrosion or interference with the pump's operation.

Figure 1:
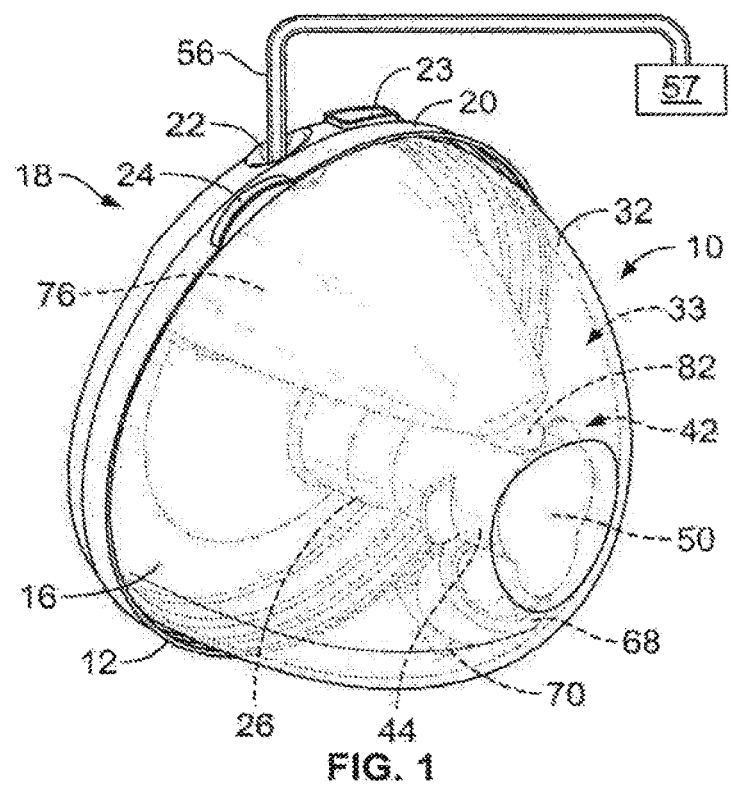
FIG. 1 is a partial sectional perspective assembly view of the breast milk collection device with self-contained reservoir of the present disclosure, illustrating the funnel shaped breast adapter, and submersible barrier and one-way valve located in the reservoir.
Figure 2:
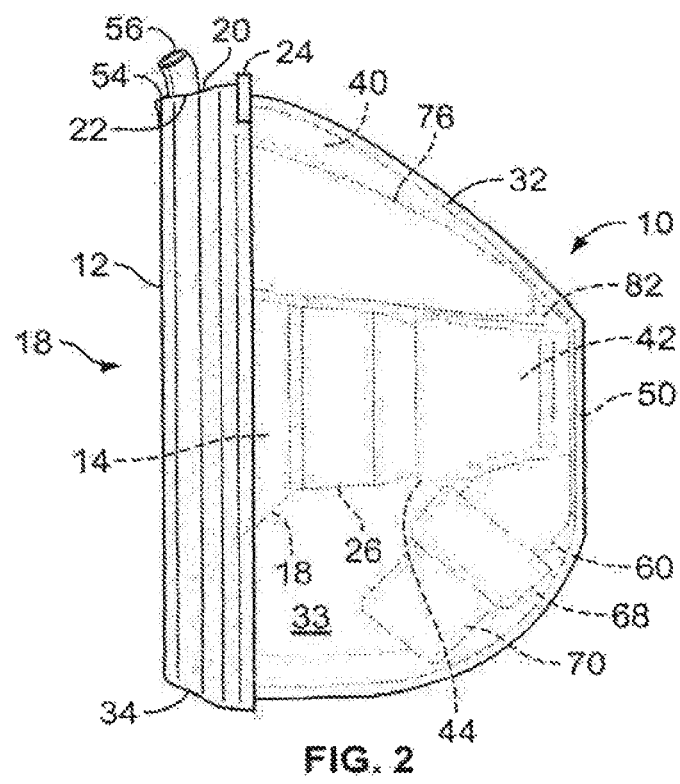
FIG. 2 is a partial section elevation assembly view of the breast milk collection device of FIG. 1.
Figure 3:
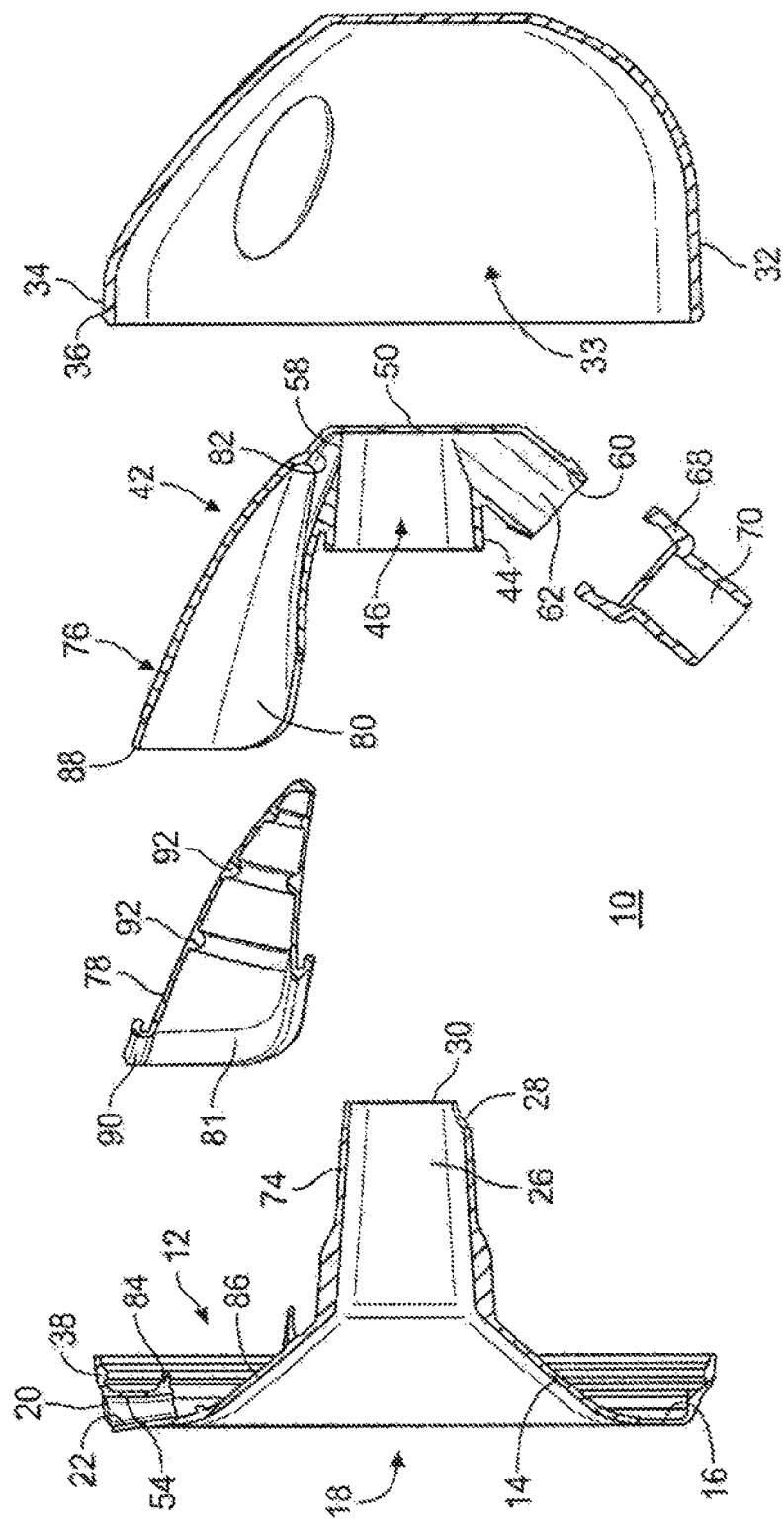
FIG. 3 is an exploded elevation cross-section view of the breast milk collection device of FIGS. 1 and 2.

Referring to FIGS. 1 and 2, the breast milk collection device 10 of the present invention includes an adaptor 12 having a funnel-shaped central portion 14 within which a lactating woman's breast is to be inserted, and a wall or plate 16 circumscribing the wide end 18 of the adaptor 12. Plate 16 includes an outer rim 20 extending inwardly from the outer edge of plate 16. Outer rim 20 includes an opening 22 and a tab 24 for purposes to be explained. Outer rim 20 also includes a second opening comprising a pour spout 23 that communicates with the interior 40 (FIG. 2) of reservoir 33, allowing milk to be poured from the reservoir into a suitable container. The funnel-shape of portion 14 of adaptor 12 is selected and can be adapted to accommodate a wide variety of female breast shapes and sizes.

Figure 4:
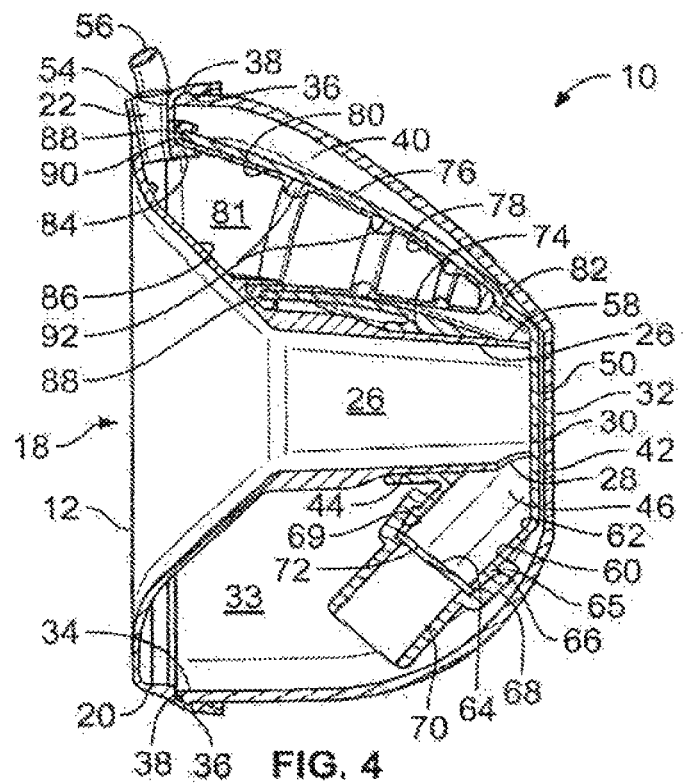
FIG. 4 is a cross-section assembly view of the breast milk collection device shown in FIGS. 1, 2 and 3, showing the flexible barrier in its expanded position.

Referring to FIG. 4, the funnel shaped portion 14 of adaptor 12 progressively narrows and terminates at a hollow drip tube 26 having an aperture 28 adjacent the distal end 30 of drip tube 26. In the illustrated embodiment, drip tube 26 is made of a material that prevents the drip tube from collapsing when vacuum pressure is applied to the drip tube.

Drip tube 26 receives milk expressed from the lactating woman's breast during the pumping operation, to be explained. A reservoir housing 32 forms a reservoir 33, and the housing 32 has a rim 34 including a radially outward extending bead 36 that removably engages circular groove 38 in outer rim 20 of adaptor 12, providing a snap-fit removable connection between reservoir housing 32 and adaptor 12, as shown in FIG. 4, to form reservoir 33. Breast milk flowing through funnel shaped adaptor 12 also flows to drip tube 26, and through aperture 28 and eventually into the reservoir 33, where the breast milk fills the reservoir. The drip tube 26 and funnel shaped adaptor 12 protrude a distance into the confines of the reservoir's internal volume 40, which can be an inch or more, giving the nipple of the breast room to elongate in a forward motion during pumping, providing an optimal nipple orientation for milk expression. The compact shape of the reservoir housing 32 allows the entire device 10 to fit discreetly within a woman's standard or nursing brassiere. The adaptor 12 and reservoir 33 comprise a single self-contained unit that does not depend on external milk collection containers.

As seen in FIGS. 1-6, a valve assembly 42 is adapted to frictionally fit tightly over the distal end 30 of drip tube 26 and control the flow of breast milk from adaptor 12 to reservoir 33. Valve assembly 42 in the illustrated embodiment includes a sleeve 44 having a hollow portion 46 formed within the sleeve 44. A wall 50 closes one end of hollow portion 46.

The opening or aperture 22 of rim 20 of adapter 12 includes a flared upper open end. The opening 22 is adapted to receive and frictionally hold a hollow vacuum tube 56 that leads to a source of cyclic vacuum force and relief pressure 57 (FIG. 1), as explained more fully in U.S. Pat. Nos. 7,559,915 and 8,118,772. The lower end of aperture 22 communicates with the interior chamber 81 of flexible barrier 78, as will be explained.

As shown in FIG. 4 extending downward from aperture 28 in drip tube 26 is a tubular valve mounting assembly 60 comprising a hollow interior chamber 62, communicating with the interior of hollow drip tube 26 and an opening 64. Opening 64 is circumscribed by a rim structure 65 having an outer circular surface 66.

In the illustrated embodiment of FIGS. 1-8, a valve mount 68 has an interior circular surface 69 constructed to frictionally and tightly fit over outer circular surface 66 of rim structure 65. A one way valve element 70 is mounted over opening 72 of mount 68 to allow breast milk to pass in one direction from the lactating woman's breast eventually into reservoir 33. The valve 70 also prevents the reverse flow of milk from the reservoir 33 into vacuum hose 56 or into drip tube 26.

In the illustrated embodiment, valve 70 is a duckbill check valve, but other one-way check valves as are known in the art may be substituted for duckbill valve 70. Duckbill valves commonly have a duckbill-shaped inner elastomeric sleeve that responds to changes in fluid pressure, both on the internal and external surfaces of the valve. In the present invention, the valve 70 comprises two soft adjacent walls, with a slit at the bottom of the valve. The slit opens when there is positive pressure or no vacuum force if the valve's outer walls are not submersed in milk. When vacuum force is applied, the two walls are "sucked" together.

As the reservoir 33 fills with collected milk and submerses the valve 70, liquid pressure surrounding the valve 70, in the absence of a vacuum, also keeps the valve 70 closed. Vacuum force causes valve 70 to close and stop milk migration back into the drip tube and barrier/valve assembly that may result from backflow milk pressure in the reservoir 33 caused by the cyclic application of vacuum force and relief pressure during the milk pumping process, thus preventing milk from the reservoir 33 from being drawn into hollow vacuum tube 56, which prevents damage to the vacuum pumping system.

When the milk pumping cycle is relieved of the vacuum force, or the source of vacuum force cycles off, valve 70 opens to allow milk to advance from drip tube 26 to the interior volume 40 of reservoir 33. The buildup of milk in interior chamber 62 of valve assembly 42, combined with positive pressure returning during the pump's positive cycle, forces duckbill valve 70 open, as the pressure behind the milk passing through valve 70 is temporarily greater than the ambient pressure of the milk in the reservoir which is acting across the duckbill shaped outer surfaces of the valve 70, so the valve 70 opens and milk flows through the valve. However, during a vacuum portion of the pumping cycle, the vacuum force is applied to the inner walls of the valve 70, and the duckbill elastomer valve 70 flexes closed, preventing the backflow of milk out of reservoir 33. Other suitable one-way check valves may be used in place of the illustrated duckbill valve 70.

The presently disclosed breast milk collection device, in an embodiment, incorporates an improved flexible barrier structure that allows vacuum pressure to be cyclically applied to the breast for the expression of milk into the reservoir 33, while at the same time prevents any of the milk in the reservoir 33 from entering the vacuum tube 56 or the vacuum pump 57. The improved barrier also continues to function when submerged in the milk in the reservoir volume 40.

Referring to FIGS. 1, 2, 4 and 6, the upper portion of valve assembly 42 comprises a rigid barrier housing 76 that encloses a flexible barrier 78 in hollow chamber 80 of barrier housing 76, as seen in FIG. 4. In the illustrated embodiment, flexible barrier 78 is made of a soft rubbery or thin plastic material that is readily collapsible and inflatable, as will be explained. Hollow chamber 80 communicates with a hollow tubular channel 82 of barrier housing 76, and tubular channel 82 communicates through aperture 58 with drip tube 26, allowing milk to flow through tubular channel 82 and into chamber 80. Hollow chamber 80, tubular channel 82, aperture 58 and hollow portion 46 of sleeve 44 combine to form a fluid passageway in valve assembly 42. Ultimately, milk in chamber 80 is conveyed to reservoir 33 upon the opening of one-way valve 70.

Figure 8:
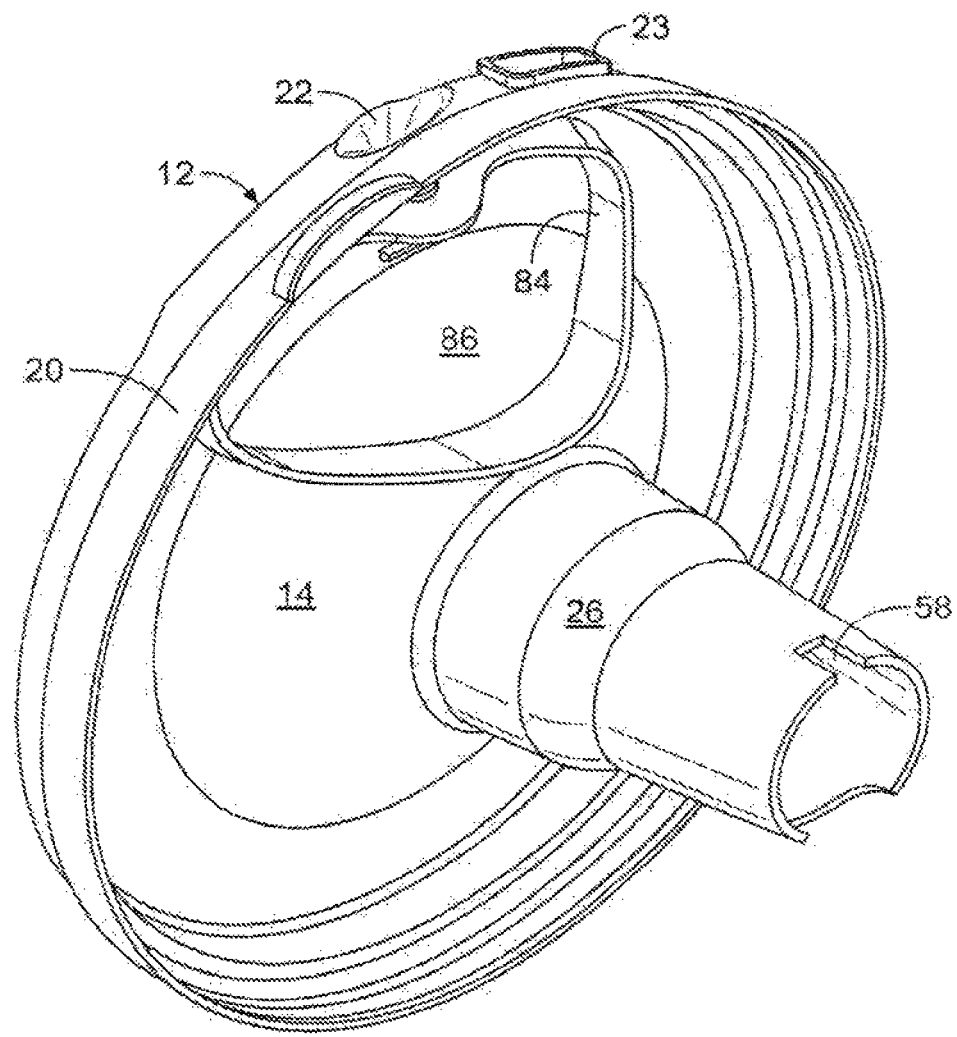
FIG. 8 is a perspective detailed view of the funnel and drip tube assembly, illustrating the rimmed flange for attachment of the barrier housing and flexible barrier to the funnel.

As seen in FIGS. 4 and 8, a somewhat oval rimmed flange 84 extends outwardly from inner face 86 of adaptor 12. The outer rim 88 of barrier housing 76 is the same somewhat oval shape as rimmed flange 84, and the outer rim 88 extends over flange 84 as seen in FIG. 4. The outer rim 90 of barrier 78 is similarly oval in shape, and is held securely between flange 84 and outer rim 88 of the barrier housing 76. Thus, a hermetic seal is formed between barrier 78, the barrier housing 76 and reservoir 33. As seen in FIG. 4, vacuum tube 56 extends into opening 22 such that vacuum force from vacuum source 57 (FIG. 1) is applied to the interior of barrier 78, but the vacuum force and subsequent relief pressure from vacuum tube 56 are completely isolated from interior chamber 80 of barrier housing 76. The vacuum force and relief pressure are also isolated from reservoir 33. This structure prevents milk from reservoir 33 or hollow chamber 80 from migrating to vacuum tube 56 or vacuum source 57. In the illustrated embodiment, the exterior surface of flexible barrier 78 is shaped so that the exterior surface lies adjacent the interior surface of barrier housing 76 when flexible barrier 78 is in its inflated or expanded position, as seen in FIG. 4. In one embodiment of flexible barrier 78, a plurality of strengthening ribs 92 extend around the inner surface of barrier 78, as seen in FIG. 4. Other variations in flexible barrier wall thicknesses and shapes may be utilized in other embodiments of the invention, to accommodate various performance attributes that may be desired for suction sources 57 produced by different manufacturers.

Vacuum tube 56 is manually removed from opening 22 of rim 20 of adaptor 12, where air is sucked from chamber 81 of flexible barrier 80 by applying a slight upward axial force to tube 56. Reservoir housing 32 is removed from adaptor 12 by applying manual pressure to tab 24 of the adaptor, and applying an opposite manual force to reservoir housing 32 to release bead 36 from groove 38. The valve assembly 42 is then removed from adaptor 12 by applying manual force that overcomes the friction fit that holds valve assembly 42 to drip tube 26. Mount 68 of one-way valve 70 is axially removed from rim structure 65, removing valve 70 for cleaning.

Upon removal of valve assembly 42 from the distal end 30 of drip tube 26, barrier housing 76 and flexible barrier 78 are also disengaged from rimmed flange 84, allowing barrier 78 to be manually axially removed from hollow chamber 80. This allows the chamber 80 of rigid barrier housing 76 and the flexible barrier 78 to be separately cleaned. After cleaning of all of the separated elements, including valve 70, the flexible barrier is reinserted in the chamber 80 of rigid barrier housing 76, following which valve assembly 42 with valve 70 attached to mount 68 is reinserted over drip tube 26. Reservoir housing 32 is then reattached to adaptor 12 by snapping bead 36 into groove 38 of adaptor rim 20. Vacuum hose 56 is reinserted into opening 22, and the assembled breast milk collection device is ready for additional use.

In operation, the breast milk collection device 10 is assembled as shown in FIGS. 2 and 4. Valve assembly 42 is attached over the distal end 30 of drip tube 26, and then hollow vacuum tube 56 is inserted into flared upper end 54 of opening 22 of rim 20 of adaptor 12, where tube 56 communicates with chamber 81 of the flexible barrier 78. Vacuum tube 56 is manually manipulated into the adaptor's funnel's opening 22 until the tube 56 wedges itself into the opening. Next, reservoir housing 32 is inserted into rim 20 of plate 16 until bead 36 is fully seated in groove 38. Tab 24 is used to grip adaptor 12 when attaching reservoir housing 32 to adaptor 12, and also to remove the reservoir housing from the adaptor.

The end of vacuum tube 56 shown in FIGS. 1 and 4 is now wedged into a frictional fit into the flared upper end 54 of opening 22, which holds tube 56 in tight engagement with rim 20 of adaptor 12. The tube 56 extends downward such that the hollow interior of tube 56 communicates with the interior chamber 81 of flexible barrier 78.

One or a pair of milk collection devices 10 are then inserted onto the breast and into one or each of the cups of the nursing or standard brassiere of the lactating woman to be held in place there. One or both breasts will firmly fit into a respective funnel-shaped central portion 14 of each adaptor 12. The contact between the breast and the adaptor 12 creates a seal, whereby the vacuum force applied to the outer end of the breast does not escape between the breast and the adaptor.

The outer end of hollow vacuum tube 56 is attached to cyclical operating vacuum pump 57 (FIG. 1) as is known in the art. The pump furnishes alternating vacuum force and relief to ambient pressure to the interior of tube 56.

Figure 6:
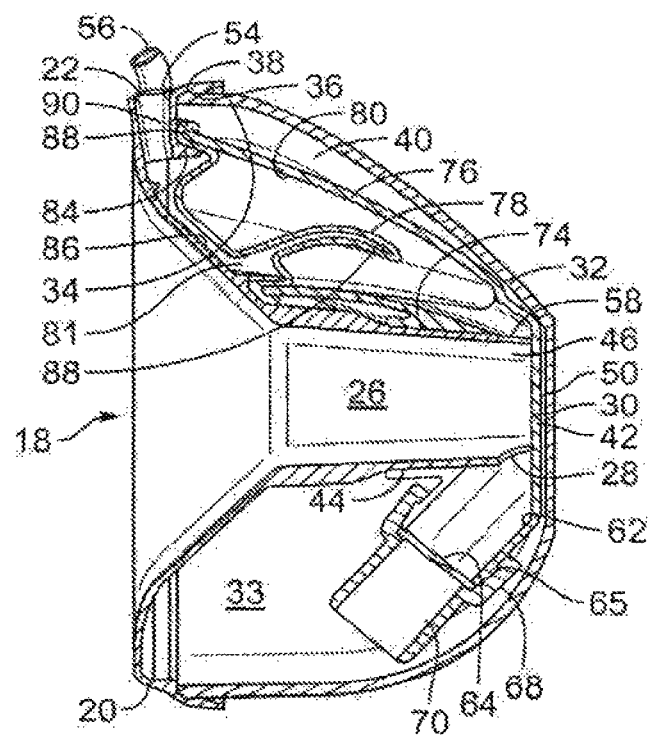
FIG. 6 is a cross-section assembly view of the breast milk collection device shown in FIG. 4, illustrating the flexible barrier in its contracted position.
Figure 5:
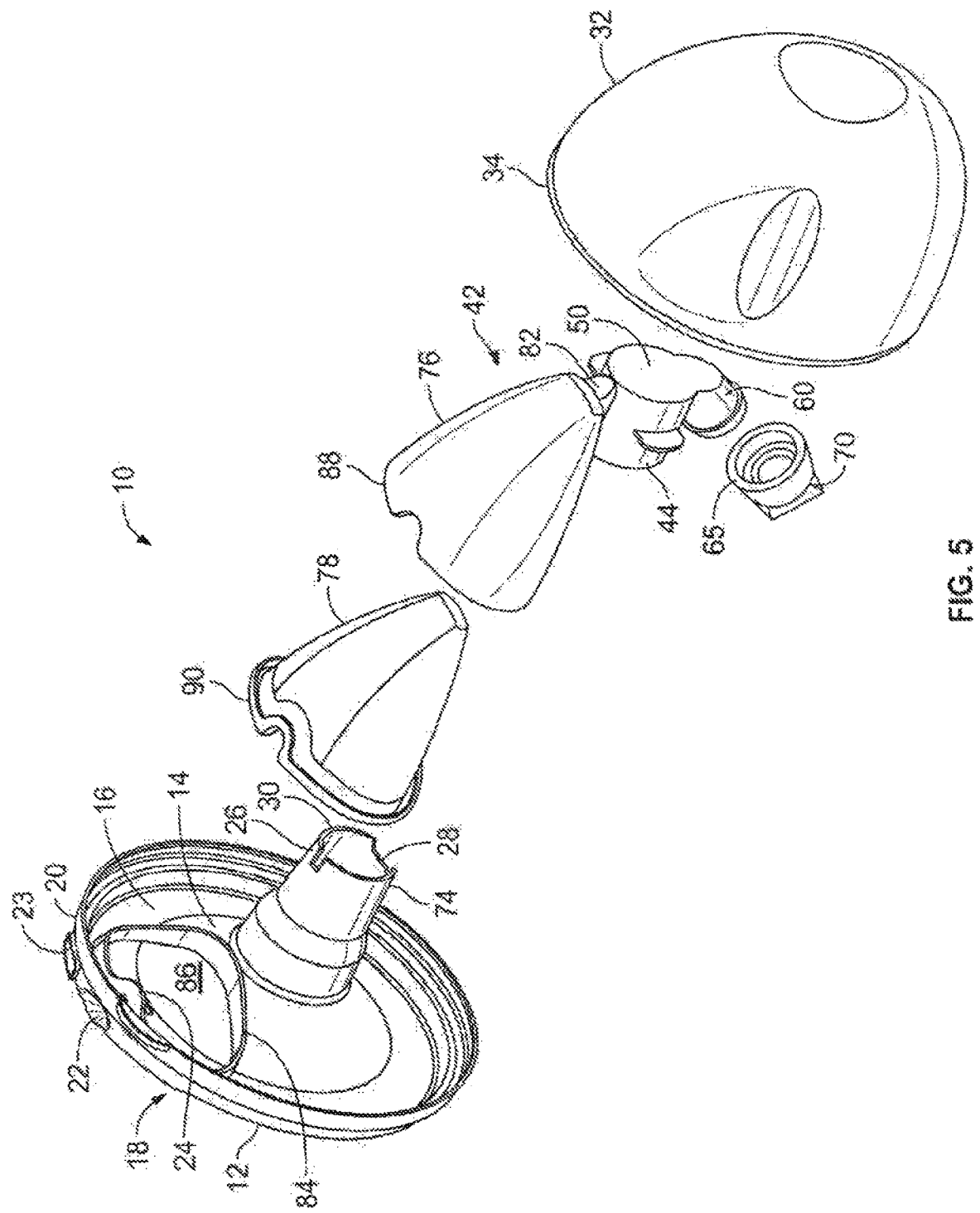
FIG. 5 is an exploded perspective view of the breast milk collection device shown in FIG. 4.
Figure 7:
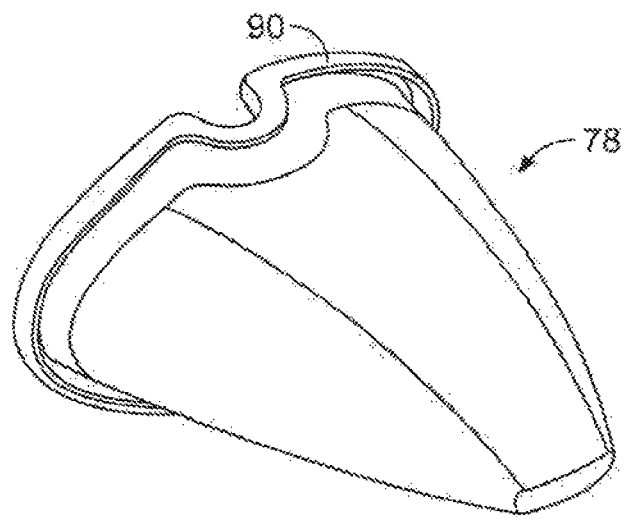
FIG. 7 is a perspective detail view of the flexible barrier.

The cyclical vacuum force is communicated from vacuum tube 56 directly to the interior chamber 81 of flexible barrier 78, which causes barrier 78 to collapse, as seen in FIG. 6, and a vacuum is created on the opposite side of barrier 78. As a result of the decrease of volume of barrier 78 due to deflation, a vacuum is drawn in hollow chamber 80 of barrier housing 76, which vacuum force is transmitted to the breast through aperture 58 and through drip tube 26. The nipple of the breast extends into the drip tube 26, and milk is expressed from the breast. The cycle of applying and relieving the vacuum force on the breast causes milk to be expressed from the breast and into the drip tube. Due to the hermetic seal between flexible barrier 78, barrier housing 76 and inner face 86 of adaptor 12, no milk can migrate to vacuum tube 56, or to source of vacuum pressure 57 (FIG. 1).

Upon the relief of maximum negative vacuum force in the interior chamber 81 of flexible barrier 78 during the cyclic operation of vacuum source 57, the inherent forces acting on flexible barrier 78 cause the barrier to expand to its natural shape, as seen in FIG. 4, simultaneously increasing the pressure in hollow chamber 80 of barrier housing 76.

At this time, milk expressed during the previous cycle and any remnants from previous cycles migrate through the fluid passageway formed by interior chamber 62 of valve assembly 42 and valve 70 to reservoir 33 where the milk is stored, and little or no milk remains in drip tube 26 or in interior chamber 62 of valve assembly 42.

As the above milk-expression cycles repeat, the fluid level in internal volume 40 of reservoir 33 rises eventually to a level above the location of one-way valve 70. The then submerged valve 70 continues to function normally as the level of milk in reservoir 33 rises and submerses the valve. As the milk in reservoir 33 continues to rise, the outer submerged walls of valve 70 are collapsed together by the vacuum force during the negative cycle and are also being compressed by the liquid pressure of the milk in the reservoir 33 when the vacuum pump is turned off, thus closing the valve and preventing the backflow of milk into drip tube 26 and adaptor 12, even during the absence of vacuum force in hollow vacuum hose 56. This allows the maximum internal volume 40 of reservoir 33 to be utilized, thus collecting the maximum amount of expressed milk.

As the milk in reservoir 33 rises beyond the level of drip tube 26, the milk is prevented from migrating into chamber 80 of rigid barrier housing 76, and the hermetic seal between rims 88, 90 and rimmed flange 84 (FIGS. 4, 6) prevents any milk from entering vacuum tube 56. As a result, there is no impediment to the cyclical expansion and contraction of flexible barrier 78 as negative vacuum force and alternate relief pressure is cyclically applied and relieved. The milk can rise to the upper level of the reservoir without interfering with the operation or efficiency of flexible barrier 78.

In the disclosed embodiment of FIGS. 1-8, milk is withdrawn from reservoir 33 by removing the breast milk collection device 10 from the mother's existing or nursing brassiere, and then inverted. The milk in the reservoir 33 pours out of spout 23 and is transferred into a suitable container (not shown). The hollow vacuum tube 56 can remain attached to adaptor 12 in aperture 22 while pouring the milk from spout 23, or the tube 56 can be removed. The reservoir housing 32 remains attached to adaptor 12 as milk is poured from spout 23.

During the pouring operation, ambient air enters reservoir 33 through valve 70. This ambient air replaces the volume of milk poured from the reservoir 33, such that the milk pours out of spout 23 in a smooth, even and uninterrupted flow stream.

Figure 9:
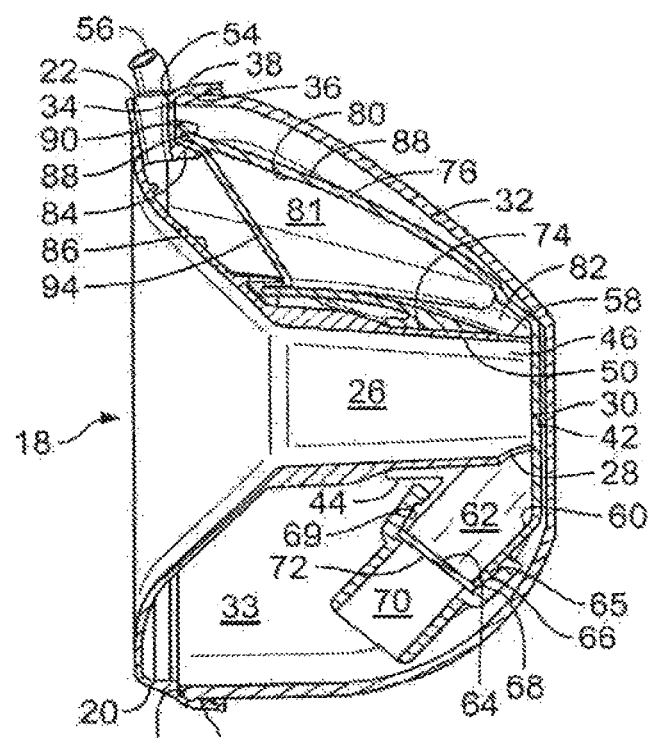
FIG. 9 is a cross-section elevation view of an alternate embodiment where a rigid hydrophobic filter replaces the flexible barrier.

An alternate embodiment of the present disclosure is illustrated in FIG. 9, which shows a rigid hydrophobic, fixed shape filter 94 replacing the flexible barrier assembly of FIGS. 1-8 in barrier housing 76. The filter 94 is made of polytetrafluorethylene (PTFE) material or any other suitable hydrophobic filter material as is known in the art, which is non-permeable to liquids, but allows air to pass through the filter without the liquid plugging up the filter. The filter 94 is hermetically sealed at its edges between rimmed flange 84 of adaptor 12 and outer rim 88 of barrier housing 76, as previously described in association with FIG. 4.

During cyclical operation of vacuum source 57 (FIG. 1) negative vacuum force or relieved air or positive pressure, can pass through filter 94, applying cyclic pumping pressure to hollow chamber 80 of barrier housing 76 and ultimately to the breast to express milk as previously described. As milk enters hollow chamber 80 of the barrier housing, the liquid milk cannot pass through filter 94, while the flow of air through the filter is not impeded. Thus, milk cannot flow into vacuum tube 56 or to pump 57 providing the source of vacuum force and relief pressure.

The foregoing description of illustrated embodiment of the invention has been presented for purposes of illustration and description, and is not intended to be exhaustive or to limit the invention to the precise form disclosed. The description was selected to best explain the principles of the invention and practical application of these principles to enable others skilled in the art to best utilize the invention in various embodiments and various modifications as are suited to the particular use contemplated. It is intended that the scope of the invention not be limited by the specification, but be defined by the claims set forth below.

What is claimed:

1. A breast milk collection device, comprising:
    an adaptor adapted at one end to receive a woman's breast therein, a second end of said adaptor communicating with a reservoir, said reservoir adapted to receive breast milk from said adaptor;
    said reservoir having an internal volume, said second end of said adaptor extending into said internal volume of said reservoir;
    a source of cyclical application and relief of vacuum force in communication with said adaptor, said cyclical application and relief of vacuum force adapted to be cyclically applied to the woman's breast located in said adaptor for the expression of breast milk into said adaptor;
    a valve assembly in communication with said adaptor, said valve assembly including a fluid passageway and a valve element extending into said reservoir, said valve element adapted to permit breast milk to enter said reservoir through said fluid passageway and to submerge said valve element in said milk, said valve element adapted to prevent breast milk from passing from said reservoir volume to said fluid passageway;
    said valve assembly further including a rigid barrier housing having a first hollow chamber inside the rigid barrier housing, the rigid barrier housing extending into said internal volume of said reservoir, the first hollow chamber of said rigid barrier housing having a first opening at a first end of said first hollow chamber, said first opening providing fluid communication between said fluid passageway and said first hollow chamber;
    said first hollow chamber having a second opening opposite said first opening, said second opening defined by a rim of the second opening of the rigid barrier housing, said rim circumscribing said second opening;
    said first and second openings of said rigid barrier housing separated by an uninterrupted linear distance, said linear distance providing an uninterrupted linear fluid path between said first opening and said second opening of said rigid barrier housing;
    a hydrophobic barrier connected to said adaptor, said hydrophobic barrier extending across and connected to said rim of said second opening forming a hermetic seal between the adaptor and the rim, said hydrophobic barrier having a first surface in communication with said source of cyclical application and relief of vacuum force and relief pressure and a second surface adapted to be in contact with breast milk in said fluid passageway, said hydrophobic barrier isolating said source of cyclical application and relief of vacuum force from said reservoir and isolating said source of cyclical application and relief of vacuum force from the breast milk receiving portions of said valve assembly;
    said hydrophobic barrier allowing said cyclical application and relief of vacuum force to pass through said hydrophobic barrier, said hydrophobic barrier adapted to prevent breast milk from flowing through said hydrophobic barrier from said first hollow chamber to said source of cyclical application and relief of vacuum force.

2. The breast milk collection device of claim 1, wherein:
    said hydrophobic barrier is composed of polytetrafluoroethylene (PTFE).

3. The breast milk collection device of claim 1, wherein:
    said source of cyclical application and relief of vacuum force is provided through a tube connected to and extending through said adaptor;
    said hydrophobic barrier defining said first hollow chamber between said rigid hydrophobic barrier housing and said hydrophobic barrier, said tube isolated from said first hollow chamber;
    said hydrophobic barrier defining a second hollow chamber between said hydrophobic barrier and said adaptor, said second hollow chamber in communication with said tube;
    said tube providing said source of cyclical application and relief of vacuum force in communication with said second hollow chamber;
    said source of cyclical application and relief of vacuum force producing a vacuum force in said first hollow chamber and in said fluid passageway when said vacuum force is applied to said second hollow chamber;
    said source of cyclical application and relief of vacuum force relieving the vacuum force in said first hollow chamber and in said fluid passageway when said relief of vacuum force is applied to said second hollow chamber.

* * * * *